(12) United States Patent
Guminski et al.

(10) Patent No.: US 8,664,409 B2
(45) Date of Patent: Mar. 4, 2014

(54) PROCESS FOR THE PREPARATION OF (POLY) AMINOALKYLAMINOACETAMIDE DERIVATIVES OF EPIPODOPHYLLOTOXIN USEFUL FOR THEIR APPLICATIONS IN THERAPEUTICS AS ANTICANCER AGENT

(75) Inventors: Yves Guminski, Lagarrigue (FR); Martial Grousseaud, Castres (FR); Thierry Imbert, Viviers les Montagnes (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 308 days.

(21) Appl. No.: 12/733,864

(22) PCT Filed: Sep. 23, 2008

(86) PCT No.: PCT/FR2008/051700
§ 371 (c)(1),
(2), (4) Date: Mar. 24, 2010

(87) PCT Pub. No.: WO2009/050365
PCT Pub. Date: Apr. 23, 2009

(65) Prior Publication Data
US 2012/0022273 A1    Jan. 26, 2012

(30) Foreign Application Priority Data
Sep. 25, 2007  (FR) ...................... 07 06693

(51) Int. Cl.
*C07D 307/77* (2006.01)
(52) U.S. Cl.
USPC .......................................... 549/298
(58) Field of Classification Search
USPC .......................................... 549/298
See application file for complete search history.

(56) References Cited

U.S. PATENT DOCUMENTS 6,521,252 B1 *  2/2003  Byk et al. ..................... 424/450

FOREIGN PATENT DOCUMENTS

| WO | WO 98/34910 | | 8/1998 | |
| WO | WO 2004/073375 | * | 9/2004 | ........... C07D 493/02 |
| WO | WO 2004/073375 | | 11/2004 | |
| WO | WO 2005/100363 | * | 10/2005 | ........... C07D 493/04 |

OTHER PUBLICATIONS

Jiang et al. Journal of the American Chemical Society, 2003, 125, 1877-1887.*
Montalbetti et al. Tetrahedron, 2005 61, 10827-10852.*
Kamal et al. Bioorganic and Medicinal Chemistry Letters, 1998, 8, 3097-3100.*
Andruszkiewicz, et al., Synthetic Communications, vol. 35, p. 1085-1094, 2005.
Blagbrough, et al., Tetrahedron Letters, Vo. 39, p. 439-442, 1998.
Guianvarc'h, et al., Journal Medicinal Chemistry, vol. 47, p. 2365-2374, 2004.
Montalbette, et al., Tetrahedron, vol. 61, Report No. 740, p. 10827-10852, 2005.
Nakagawa-Goto, et al. Bioorganic and Medicinal Chemistry Letter 15, p. 235-238, 2005.
Pettit, et al., Journal of Organic Chemistry, vol. 61, No. 7, p. 2322-2325, Apr. 5, 1996.
Xiao, et al., Bioorganic and Medicinal Chemistry, vol. 12, p. 3363-3369, 2004.
Zhou. Journal of Medicinal Chemistry, vol. 34, p. 3346-3350, 1991.
Byk, et al, One Pot Synthesis of Unsymmetrically Functionalized Polyamines by a Solid Phase Strategy Starting From Their Symmetrical Polyamine Counterparts, Tetrahedron Letters, vol. 38, No. 18, p. 3219-3222, May 5, 1997.
Christophe Jacopin, et al., Glycosidation of Alkylamino-Alkan-1-Ol. A Simple and Convenient Synthesis of Glycosylated Cationic Lipids, Bioorganic and Medicinal Chemistry, vol. 12, p. 1447-1450, 2002.
French Preliminary Search Report for FR0706693 of May 26, 2008.
International Search Report for PCT/FR2008/051700 of Jun. 8, 2009.
Kamal, et al, "Synthesis of 4-Beta-Amido and 4-Beta-Sulphonamido Analogues of Podophyllotoxin As Potential Antitumor Agents" Bioorganic and Medicinal Chemistry, Vo. 11, No. 23, p. 5135-5142, Nov. 17, 2003.
International Preliminary Report on Patentability with Written opinion for PCT/FR2008/051700 of May 20, 2010.

* cited by examiner

*Primary Examiner* — Nizal Chandrakumar
(74) *Attorney, Agent, or Firm* — Hueschen and Sage

(57) ABSTRACT

The present invention relates to a new process for the preparation of (poly)aminoalkylaminoacetamide derivatives of epipodophyllotoxin and salts thereof, characterized in that it comprises a step of peptide coupling of 4-amino-4'-demethylepipodophyllotoxin with an amine-containing reactant having protecting groups.

18 Claims, No Drawings

PROCESS FOR THE PREPARATION OF (POLY) AMINOALKYLAMINOACETAMIDE DERIVATIVES OF EPIPODOPHYLLOTOXIN USEFUL FOR THEIR APPLICATIONS IN THERAPEUTICS AS ANTICANCER AGENT

The present invention relates to a new process for the preparation of (poly)aminoalkylaminoacetamide derivatives of epipodophyllotoxin, of formula 1, and pharmaceutically acceptable salts thereof.

Formula 1

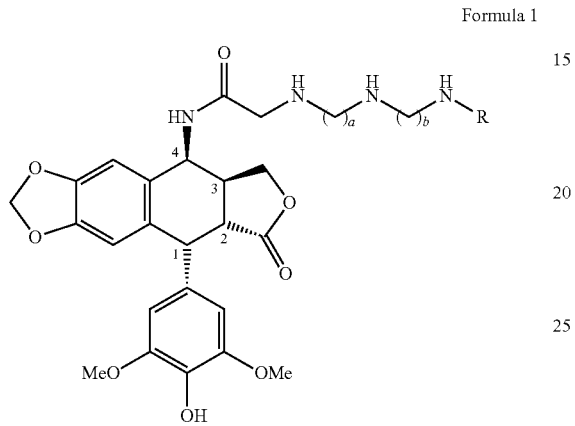

wherein R represents a hydrogen atom or a group —$(CH_2)_c$—$NH_2$, with $2 \leq a,b,c \leq 5$.

These compounds are composed of an epipodophyllotoxin-type lignan portion and a polyamine portion attached at the 4-position of the epipodophyllotoxin by way of an acetamide moiety. The presence of the polyamine chain provides the molecule with its water solubility properties, especially for its hydrochlorides, and also its especially valuable pharmacological properties in the treatment of cancers.

These compounds, which are described in patent application WO 2005/100363, are accordingly anticancer compounds that are especially useful in the treatment of solid or non-solid tumours such as melanomas, colorectal cancers, cancers of the lung, prostate, bladder, breast, uterus, stomach, pancreas, liver and ovaries and also in the treatment of leukaemias, lymphomas and myelomas, cancers of the ENT system and brain tumours. The synthesis process described in WO 2005/100363 for the preparation of compounds of formula 1 uses, as starting material, podophyllotoxin of formula 2

Formula 2

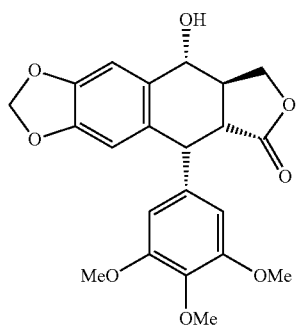

and then 4'-demethylepipodophyllotoxin of formula 3

Formula 3

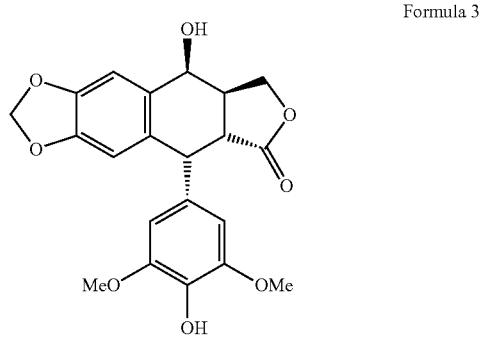

with which chloroacetonitrile is reacted in an acid medium to obtain the synthesis intermediate 4-chloroacetamido-4'-demethylepipodophyllotoxin of formula 4

Formula 4

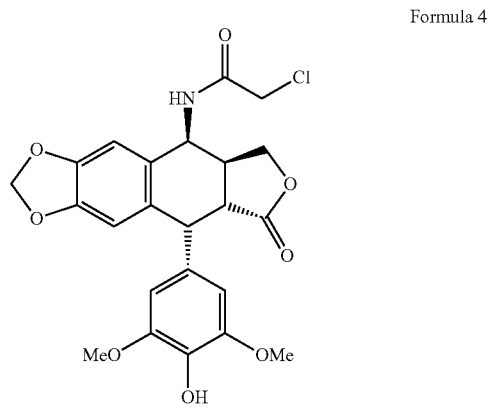

This compound is then condensed with a primary-amine-containing reactant of formula 5:

Formula 5

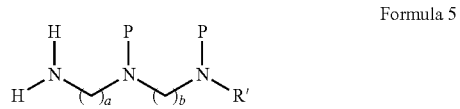

wherein R' represents a hydrogen atom or a chain —$(CH_2)_c$—NHP, wherein a, b and c are as defined hereinbefore and wherein P represents a group protecting the amine functions. Appropriate protecting groups may be a benzyl, benzyloxycarbonyl or tert-butyloxycarbonyl radical. This condensation is carried out in a mixture of solvents comprising an aprotic polar solvent (acetonitrile, DMF) in the presence of a Lewis base (triethylamine).

However, this process, besides the fact that it has a high number of steps and therefore quite a low overall yield, has two disadvantages:

On the one hand, the conditions used in patent specification WO 2005/100363 are conducive to epimerisation of the carbon in the 2-position of the epipodophyllotoxin derivative of formula 1, resulting in a cis-lactone form, referred to as the "picro" form, of formula 7

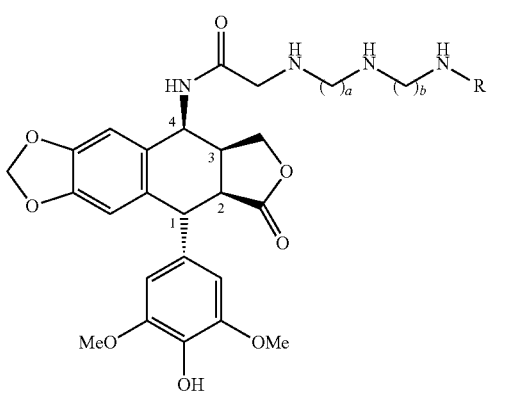

Formula 7

Purification of the desired trans-lactone product is therefore difficult and necessitates laborious and costly chromatography operations.

On the other hand, the method described hereinbefore also produces bis-alkylation type by-products, as a result of reaction of another molecule of 4-chloroacetamido-4'-demethyl-epipodophyllotoxin with the secondary amine group formed of the product of formula 1 in protected form. The use of an excess of primary-amine-containing reactant of formula 5 is then necessary for conversion of the starting materials that is as complete as possible whilst minimising the by-products obtained, which necessitates a difficult step of recovering the excess amine, making this process uneconomical.

The Applicant has found, in unexpected manner, that as a result of condensing—by peptide coupling—polyaminoacetic acid of formula 6, wherein R' represents a hydrogen atom or a chain —$(CH_2)_c$—NHP, a, b and c having the same values as hereinbefore and wherein P represents the group protecting the amine functions, with 4-amino-4'-demethylepipodophyllotoxin of formula 4bis, there was obtained a coupling compound in a very good state of purity without using an excess of reactant. The reaction takes place with a good yield so as to yield, after deprotection of the protecting groups carried by the nitrogen atoms, (poly)aminoalkylaminoacetamide compounds of epipodophyllotoxin, of formula 1, whose water-soluble hydrochlorides are useful for their application as anticancer agents.

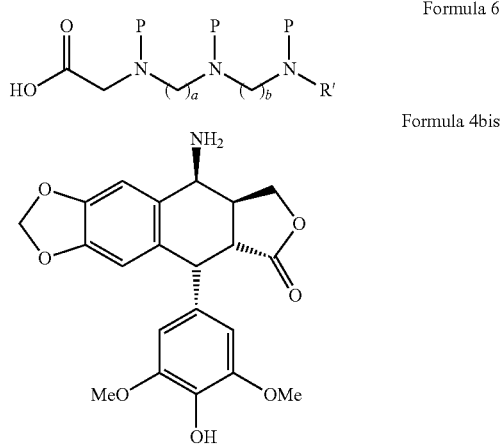

Formula 6

Formula 4bis

The present invention accordingly relates to a new process for the synthesis of compounds of formula 1 and pharmaceutically acceptable salts thereof, starting from 4-amino-4'-demethylepipodophyllotoxin of formula 4bis and comprising a step of peptide coupling of the latter with a substituted acetic acid of formula 6.

The process is preferably applied to the preparation of compounds of formula 1 in hydrochloride form.

Preference is further given to the protecting groups used in the compound of formula 6 being benzyloxycarbonyl or t-butyloxycarbonyl groups.

4-Amino-4'-demethylepipodophyllotoxin of formula 4bis is a known intermediate (*J. Med. Chem.* 2004, 47, 2365-2374, and *J. Med. Chem.* 1991, 34, 3346-3350) which can be prepared by the synthesis process described in patent application WO 2007/010007. Introduction of the acetic moiety onto the polyamine portion of compound 5 to obtain compound 6, which will then be condensed with 4-amino-4'-demethylepipodophyllotoxin of formula 4bis, accordingly represents an especially valuable strategy.

In the compounds of formula 6, the acetic moiety is supplied by reaction of the primary amine portion of (poly)aminoalkylamino derivatives of formula 5 with an alkyl haloacetate. There will preferably be used ethyl bromo-, chloro- or iodo-acetate. Other methods of introducing the acetic moiety may also be used, for example reductive amination with the aid of a glyoxylic acid derivative. Hydrolysis of the ester function to an acid can be carried out in a basic medium such as dilute sodium hydroxide solution.

The compounds of formula 5 are obtained in the manner described in the publication: *Tet. Lett.* 1998, 39,439. A particular example of the use of that synthesis is given in Example 27 of the patent application WO 2005/100363.

Peptide coupling of that acetic intermediate 6 with 4-amino-4'-demethylepipodophyllotoxin of formula 4bis makes it possible simultaneously to proceed in a neutral, and therefore non-epimerising, medium and to provide a purer product which does not require the chromatographic work that is indispensable to the strategy as described in WO 2005/100363.

The great variety of peptide coupling methods described in the literature such as, for example, in the journal: *Tet.* 2005, 61, 10827 leaves the choice to the person skilled in the art to apply the method that is most efficient and that provides the purest compound (for example, methods using: DCC, mixed anhydrides, CDI, BOP and its derivatives, TBTU). By way of example, the process using activation by TBTU (O-benzotriazol-1-yl-N,N,N',N'-tetramethyluronium tetrafluoroborate) (J.O.C. 1996, 61, 2322) has the advantage of being carried out at normal temperature in a neutral medium and of being rapid, whilst providing a clean compound whose secondary products resulting from the reagents are soluble in water in the course of extraction. Simple conventional chromatography provides, in the penultimate stage, a compound of perfect quality (purity>99%).

We will describe hereinbelow some examples showing the advantage of this process in terms of the ease of implementation and the purity of that which is obtained by means of extractive and chromatographic treatment.

The invention relates more especially to a process for the preparation of the compound of formula 1 wherein a=3, b=4 and R=—$(CH_2)_3$—$NH_2$, or 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',:6,7]naphtho[2,3-d][1,3]dioxol-5-yl]-acetamide hydrochloride, characterised in that it comprises a step of peptide coupling between 4-amino-4'-demethylepipodophyllotoxin and the compound of formula 6: {benzyloxycarbonyl-[3-(benzyloxycarbonyl-{4-[benzyloxycarbonyl-(3-benzyloxycarbonylaminopropyl)-amino]-butyl}-amino)-propyl]-amino}-acetic acid or {t-butyloxycarbonyl-[3-(t-butyloxy-carbonyl-{-4-[t-butyloxycarbonyl-(3-t-butyloxycarbonylaminopropyl)-amino]-butyl}-amino)-propyl]-amino}-acetic acid, corresponding to the compounds of formula 6 wherein a=3, b=4 and R'=—(CH$_2$)$_3$—NHP, with P being either the benzyloxycarbonyl group or the t-butyloxycarbonyl group.

The invention relates also to a process for the preparation of the compound of formula 1 wherein a=3, b=4 and R=H, or 2-[3-(4-aminobutylamino)-propylamino]-N-[9-(4-hydroxy-3,5-dimethoxyphenyl)-8-oxo-5,5a,6,8,8a,9-hexahydrofuro[3',':6,7]naphtho[2,3-d][1,3]dioxol-5-yl]-acetamide, in hydrochloride form, characterised in that it comprises a step of peptide coupling between 4-amino-4'-demethylepipodophyllotoxin and the compound of formula 6: (benzyloxycarbonyl-{3-[benzyloxycarbonyl-(4-benzyloxy-carbonylaminobutyl)-amino]-propyl}-amino)acetic acid or t-butyloxycarbonyl-{3-[t-butyloxycarbonyl-(4-t-butyloxycarbonylaminobutyl)-amino]-propyl}-amino)acetic acid, corresponding to the compounds of formula 6 wherein a=3, b=4 and R'=H, with P being either the benzyloxycarbonyl group or the t-butyloxycarbonyl group.

The invention relates also to a process for the preparation of the compound of formula 1 wherein a=4, b=4 and c=4, or 2-{4-[4-(4-aminobutylamino)-butylamino]-butylamino}-N-[9-(4-hydroxy-3,5-dimethoxyphenyl)-8-oxo-5,5a,6,8,8a,9-hexahydro-furo[3',':6,7]naphtho[2,3-d][1,3]dioxol-5-yl]-acetamide hydrochloride, characterised in that it comprises a step of peptide coupling between 4-amino-4'-demethylepipodophyllotoxin and the compound of formula 6: {benzyloxycarbonyl-[4-(benzyloxycarbonyl-{4-[benzyloxycarbonyl-(4-benzyloxycarbonylaminobutyl)-amino]-butyl}-amino)-butyl]amino}-acetic acid or {t-butyloxycarbonyl-[4-(t-butyloxycarbonyl-{4-[t-butyloxycarbonyl-(4-t-butyloxycarbonylaminobutyl)-amino]-butyl}-amino)-butyl]-amino}-acetic acid, corresponding to the compounds of formula 6 wherein a=4, b=4 and c=4, with P being either the benzyloxycarbonyl group or the t-butyloxycarbonyl group.

The invention relates also to a process for the preparation of the compound of formula 1 wherein a=4, b=3 and R=H, or 2-[4-(3-aminopropylamino)-butylamino]-N-[9-(4-hydroxy-3,5-dimethoxyphenyl)-8-oxo-5,5a,6,8,8a,9-hexahydrofuro[3',':6,7]naphtho-[2,3-d][1,3]dioxol-5-yl]-acetamide hydrochloride, characterised in that it comprises a step of peptide coupling between 4-amino-4'-demethylepipodophyllotoxin and the compound of formula 6: (benzyloxycarbonyl-{4-[benzyloxycarbonyl-(3-benzyloxy-carbonylaminopropyl)-amino]-butyl}-amino)-acetic acid or (t-butyloxycarbonyl-{-4-[t-butyloxycarbonyl-(3-t-butyloxycarbonylaminopropyl)-amino]-butyl}-amino)-acetic acid, corresponding to the compounds of formula 6 wherein a=4, b=3 and R'=H, with P being either the benzyloxycarbonyl group or the t-butyloxycarbonyl group.

Another aspect of the invention relates to a new process for the synthesis of compounds of general formula 1, characterised in that it comprises the following steps:
a) Attaching an acetic moiety to primary-amine-containing reactants of formula 5

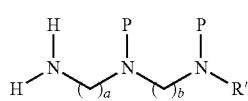

Formula 5 with the aid of an alkyl haloacetate
b) Protecting the secondary amine of the compound obtained in the preceding step a), by means of a protecting group P
c) Saponification of the compound obtained in step b), in a basic medium, to obtain the polyaminoacetic acid of formula 6
d) Peptide coupling of the polyaminoacetic acid obtained in step c), with 4-amino-4'-demethylepipodophyllotoxin of formula 4bis
e) Removing the protecting groups P from the compounds obtained in the preceding step to arrive at the compounds of general formula 1.

Preference is given to the protecting groups used in the compounds of formula 5 and in step b) being the benzyloxycarbonyl or t-butyloxycarbonyl groups.

Preference is likewise given to using, in step a), an alkyl haloacetate selected from ethyl bromo-, chloro- or iodo-acetate.

The new synthesis process is illustrated by the following reaction scheme:

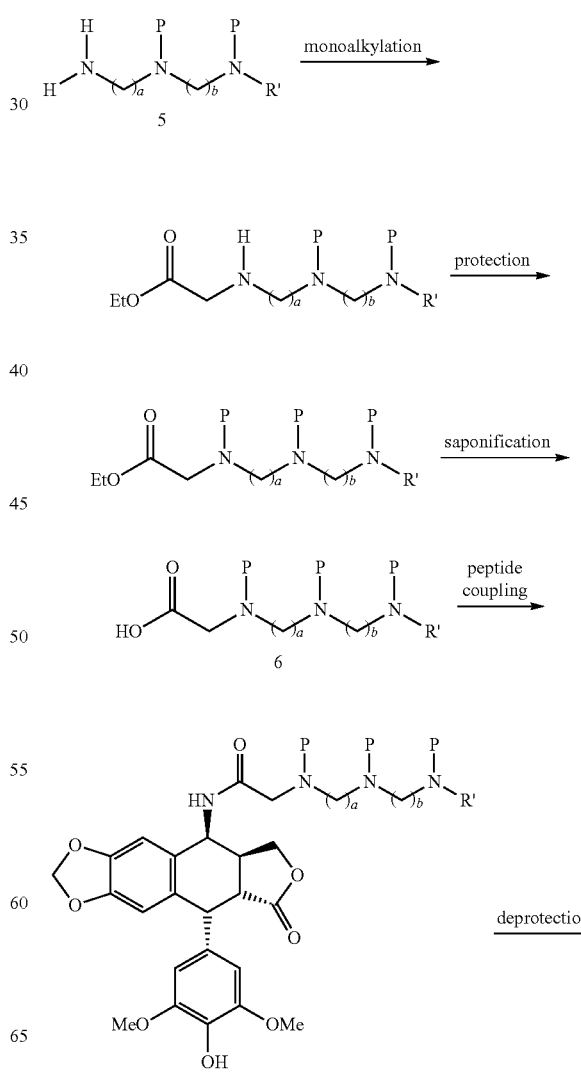

-continued

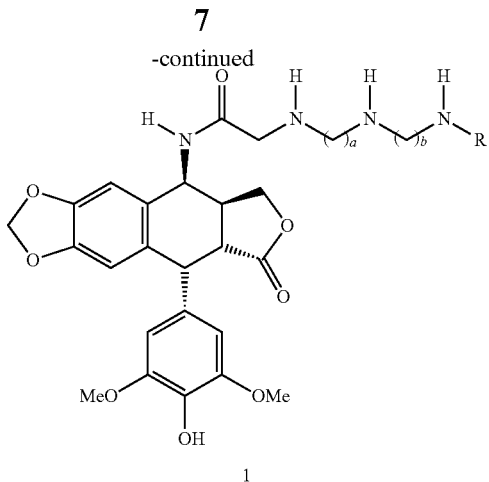

the various steps of which are described in general manner hereinbelow.

Method of Preparing Primary Amines 5

The synthesis of primary amines of formula 5 protected by protecting groups P (for example, benzyloxycarbonyl (Z)) on the nitrogen atoms which should not react is described in patent application WO 2005/100363. The benzyloxycarbonyl group represents a particular choice which is not limiting. Other protecting groups can be used within the framework of the invention. Besides substituted benzyloxycarbonyl groups, which are relatively readily cleaved, it is also possible to use butyloxycarbonyl groups, the cleaving of which in an acid medium is compatible with stability of the final compound of formula 1. Indeed, the cleaving at the end of synthesis must be compatible with the various functions in place on the final molecule. In particular, basic media are not compatible because, as mentioned hereinbefore, they bring about epimerisation of the carbon atom in the 2-position; in contrast, acid media giving rise to by-products that either are volatile or are readily separable or removable can be used.

Step 1:

In the course of this step there is carried out alkylation of the primary amine group of compound 5 with an alkyl haloacetate: for example, ethyl bromo-, chloro- or iodo-acetate, the two reactants being in stoichiometric amounts.

Step 2:

The secondary amine group obtained in the preceding step is protected by the same protecting group P as that initially used in the synthesis of the compounds of formula 5, employing customary techniques used for protection of this type of amine function. Preference is given to using the benzyloxycarbonyl or t-butyloxycarbonyl groups as protecting group. As a result, all of the identical protecting groups will be cleaved in the same step.

Step 3:

The ester obtained in the preceding step is saponified in a basic medium, for example using ethanolic sodium hydroxide solution, to obtain the compound of formula 6.

Synthesis of
4-amino-4'-demethylepipodophyllotoxin of formula 4bis

4-Amino-4'-demethylepipodophyllotoxin of formula 4bis is a known compound, the synthesis process of which has been described (*J. Med. Chem.* 2004, 47, 2365-2374, et *J. Med. Chem.* 1991, 34, 3346-3350). A new process for the synthesis of that compound, which is less dangerous and more economical and which provides a purer product forms the subject-matter of patent application WO 2007/010007.

Step 4:

In the course of this step there is carried out peptide coupling of the polyaminoacetic acid of formula 6, as synthesised above, with 4-amino-4'-demethylepipodophyllotoxin of formula 4bis. This coupling is carried out in a neutral medium and at ambient temperature.

Step 5:

The protecting groups P are removed from the compound obtained in the preceding step, according to customary deprotection techniques, to result in the compound of formula 1.

The invention relates more especially to the process for the preparation of a compound of formula 1 wherein a=3, b=4 and R=—(CH$_2$)$_3$—NH$_2$, or 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide, in hydrochloride form, characterised in that it comprises the following steps:

a) Attaching an acetic moiety to the benzyl ester of {4-[(3-aminopropyl)-benzyloxycarbonylamino]butyl}-(3-benzyloxycarbonylaminopropyl)-carbamic acid benzyl ester or tri-BOC-spermine with the aid of ethyl bromoacetate to obtain [3-(benzyloxycarbonyl-{-4-[benzyloxycarbonyl-(3-benzyloxycarbonyl-aminopropyl)-amino]-butyl}-amino)-propyl]-amino}-acetic acid ethyl ester or 3-(t-butyloxycarbonyl-{-4-[butyloxycarbonyl-(3-t-butyloxycarbonylaminopropyl)-amino]-butyl}-amino)-propylamino]-acetic acid ethyl ester b) Protecting the secondary amine of the compound obtained in the preceding step a), by means of a protecting group which is either the benzyloxycarbonyl group or the t-butyloxycarbonyl group c) Saponification of the compound obtained in step b), in a basic medium, to obtain either {benzyloxycarbonyl-[3-(benzyloxycarbonyl-{4-[benzyloxycarbonyl-(3-benzyloxycarbonylaminopropyl)-amino]-butyl}-amino)-propyl]-amino}-acetic acid or {t-butyloxycarbonyl-[3-(t-butyloxycarbonyl-{-4-[butyloxycarbonyl-(3-t-butyloxycarbonylaminopropyl)-amino]-butyl}-amino)-propyl]-amino}-acetic acid d) Peptide coupling of the compounds obtained in step c), with 4-amino-4'-demethylepipodophyllotoxin e) Removing the benzyloxycarbonyl or t-butyloxycarbonyl protecting groups from the compounds obtained in step d)

The invention more especially relates also to the process for the preparation of a compound of formula 1 wherein a=3, b=4 and R=H, or 2-[3-(4-aminobutylamino)-propylamino]-N-[9-(4-hydroxy-3,5-dimethoxyphenyl)-8-oxo-5,5a,6,8,8a, 9-hexahydro-furo[3',1':6,7]naphtho[2,3-d][1,3]dioxol-5-yl]-acetamide hydrochloride, characterised in that it comprises the following steps:

a) Attaching an acetic moiety to the compound of formula 5 wherein a=3, b=4 and R'=H, with P being either the benzyloxycarbonyl group or the t-butyloxycarbonyl group, with the aid of ethyl bromoacetate b) Protecting the secondary amine of the compound obtained in the preceding step a), by means of the same protecting group as that used in step a)

c) Saponification of the compound obtained in step b), in a basic medium, to obtain the compound of formula 6 wherein a=3, b=4 and R'=H, P having the same meaning as in steps a) and b)

d) Peptide coupling of the compound obtained in step c), with 4-amino-4'-demethylepipodophyllotoxin e) Removing the benzyloxycarbonyl or t-butyloxycarbonyl protecting groups from the compounds obtained in the preceding step.

The invention relates more especially to the process for the preparation of a compound of formula 1 wherein a=4, b=4 and c=4, or: 2-{4-[4-(4-aminobutylamino)-butylamino]-butylamino}-N-{9-(4-hydroxy-3,5-dimethoxyphenyl)-8-oxo-5,5a,6,8,8a,9-hexahydro-furo[3',':6,7]naphtho[2,3-d][1,3]dioxol-5-yl}-acetamide, in hydrochloride form, characterised in that it comprises the following steps:

a) Attaching an acetic moiety to the compound of formula 5 wherein a=4, b=4 and c=4, with P being either the benzyloxycarbonyl group or the t-butyloxycarbonyl group, with the aid of ethyl bromoacetate b) Protecting the secondary amine of the compound obtained in the preceding step a), by means of a protecting group which is the same as that used in step a)

c) Saponification of the compound obtained in step b), in a basic medium, to obtain the compound of formula 6 wherein a=4, b=4 and c=4, P having the same meaning as in steps a) and b)

d) Peptide coupling of the compound obtained in step c), with 4-amino-4'-demethylepipodophyllotoxin e) Removing the benzyloxycarbonyl or t-butyloxycarbonyl protecting groups from the compound obtained in the preceding step.

The invention relates more especially to the process for preparation of a compound of formula 1 wherein a=4, b=3 and R=H, or 2-[4-(3-aminopropylamino)-butylamino]-N-[9-(4-hydroxy-3,5-dimethoxyphenyl)-8-oxo-5,5a,6,8,8a,9-hexahydrofuro[3',':6,7]-naphtho[2,3-d][1,3]dioxol-5-yl]-acetamide hydrochloride, characterised in that it comprises the following steps:

a) Attaching an acetic moiety to the compound of formula 5 wherein a=4, b=3 and R'=H, with P being either the benzyloxycarbonyl group or the t-butyloxycarbonyl group, with the aid of ethyl bromoacetate b) Protecting the secondary amine of the compound obtained in the preceding step a), by means of a protecting group which is the same as that used in step a)

c) Saponification of the compound obtained in step b), in a basic medium, to obtain the compound of formula 6 wherein a=4, b=3 and R'=H, P having the same meaning as in steps a) and b)

d) Peptide coupling of the compound obtained in step c), with 4-amino-4'-demethylepipodophyllotoxin e) Removing the benzyloxycarbonyl or t-butyloxycarbonyl protecting groups from the compound obtained in the preceding step The invention relates also to a process for the preparation of intermediates of general formula 6

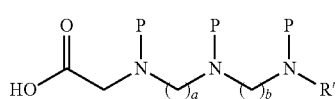

Formula 6 characterised in that it comprises the following steps:

a) Attaching an acetic moiety to the primary amines of formula 5

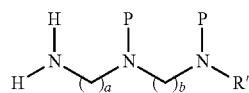

Formula 5 with the aid of an alkyl haloacetate b) Protecting the secondary amine of the compound obtained in the preceding step a), by means of a protecting group P c) Saponification of the compound obtained in step b), in a basic medium, to obtain the polyaminoacetic acid of formula 6

Preference is given to the alkyl haloacetate used in step b) being selected from ethyl bromo-, chloro- or iodo-acetate.

Preference is likewise given to the protecting groups of the compounds of formula 5 and those used in step b) being the benzyloxycarbonyl or t-butyloxycarbonyl groups.

The invention more especially relates also to a process for the preparation of the intermediate of formula 6 wherein a=3, b=4 and R'=—(CH$_2$)$_3$—NHP, with P being a benzyloxycarbonyl or t-butyloxycarbonyl group, or {benzyloxycarbonyl-[3-(benzyloxy-carbonyl-{4-[benzyloxycarbonyl-(3-benzyloxycarbonylaminopropyl)-amino]-butyl}-amino)-propyl]-amino}-acetic acid or {t-butyloxycarbonyl-[3-(t-butyloxycarbonyl-{-4-[t-butyloxycarbonyl-(3-t-butyloxycarbonyl aminopropyl)-amino]-butyl}-amino)-propyl]-amino}-acetic acid, characterised in that it comprises the following steps:

a) Attaching an acetic moiety to the primary-amine-containing reactant of formula 5:

{4-[(3-aminopropyl)-benzyloxycarbonylamino]butyl}-(3-benzyloxycarbonyl-aminopropyl)-carbamic acid benzyl ester or tri-BOC-spermine (corresponding to compounds 5 wherein a=3, b=4, R'=—(CH$_2$)$_3$—NHP, with P being either a benzyloxycarbonyl group or a t-butyloxycarbonyl group), with the aid of ethyl bromoacetate.

b) Protecting the secondary amine of the compound obtained in the preceding step a), by means of a protecting group which is the same as that selected in the preceding step.

c) Saponification of the compound obtained in step b), in a basic medium

The invention more especially relates also to a process for the preparation of the intermediate of formula 6 wherein a=3, b=4 and R'=H, with P being a benzyloxycarbonyl or t-butyloxycarbonyl group, characterised in that it comprises the following steps:

a) Attaching an acetic moiety to the primary-amine-containing reactant of formula 5 wherein a=3, b=4 and R'=H, with P being either a benzyloxycarbonyl group or a t-butyloxycarbonyl group, with the aid of ethyl bromoacetate.

b) Protecting the secondary amine of the compound obtained in the preceding step a), by means of a protecting group which is the same as that selected in the preceding step.

c) Saponification of the compound obtained in step b), in a basic medium

The invention relates also to a process for the preparation of the intermediate of formula 6 wherein a=4, b=4 and c=4, with P being a benzyloxycarbonyl or t-butyloxycarbonyl group, characterised in that it comprises the following steps:

a) Attaching an acetic moiety to the primary-amine-containing reactant of formula 5 wherein a=4, b=4 and c=4, with P being either a benzyloxycarbonyl group or a t-butyloxycarbonyl group, with the aid of ethyl bromoacetate.

b) Protecting the secondary amine of the compound obtained in the preceding step a), by means of a protecting group which is the same as that selected in the preceding step.

c) Saponification of the compound obtained in step b), in a basic medium

The invention more especially relates also to a process for the preparation of the intermediate of formula 6 wherein a=4, b=3 and R'=H, with P being a benzyloxycarbonyl or t-butyloxycarbonyl group, characterised in that it comprises the following steps:

a) Attaching an acetic moiety to the primary-amine-containing reactant of formula 5 wherein a=4, b=3 and R'=H, with P being either a benzyl-oxycarbonyl group or a t-butyloxycarbonyl group, with the aid of ethyl bromoacetate.

b) Protecting the secondary amine of the compound obtained in the preceding step a), by means of a protecting group which is the same as that selected in the preceding step.

c) Saponification of the compound obtained in step b), in a basic medium

The invention relates also to use of the compounds of general formula 6 in the preparation of compounds of general formula 1.

The invention relates also to the following compounds as new products:

(Benzyloxycarbonyl-{3-[benzyloxycarbonyl-(4-benzyloxycarbonylamino-butyl)-amino]-propyl}-amino)-acetic acid of the following formula:

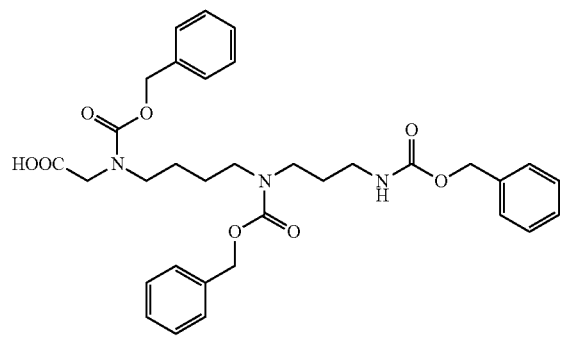

(Benzyloxycarbonyl-{4-[benzyloxycarbonyl-(3-benzyloxycarbonylamino-propyl)-amino]-butyl}-amino)-acetic acid of the following formula:

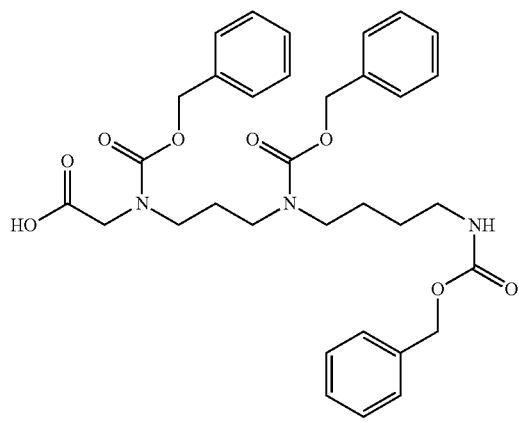 [SMILES: O=C(O)CN(CCCN(CCCCNC(=O)OCc1ccccc1)C(=O)OCc1ccccc1)C(=O)OCc1ccccc1]

(tert-Butoxycarbonyl-{3-[tert-butoxycarbonyl-(4-tert-butoxycarbonylamino-butyl)-amino]-propyl}-amino)-acetic acid of the following formula:

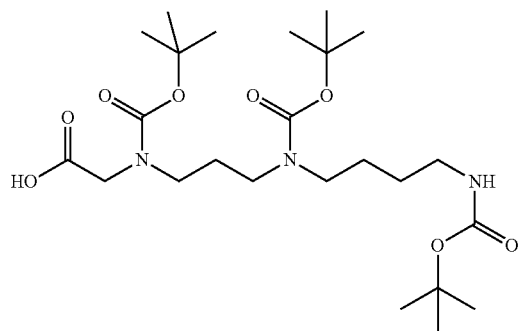 [SMILES: CC(C)(C)OC(=O)NCCCCN(CCCN(CC(=O)O)C(=O)OC(C)(C)C)C(=O)OC(C)(C)C]

(tert-Butoxycarbonyl-{-4-[tert-butoxycarbonyl-(3-tert-butoxycarbonylamino-propyl)-amino]-butyl}-amino)-acetic acid of the following formula:

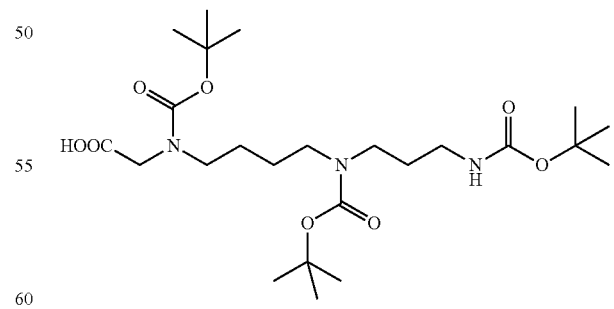

The Examples given hereinbelow serve to illustrate the process of the invention without, however, limiting the scope thereof.

A) Method Using Benzyloxycarbonyl Groups.

EXAMPLE 1

Preparation of 2-[3-(4-aminobutylamino)-propylamino]-N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-acetamide, in hydrochloride form (a=3, b=4, R=H)

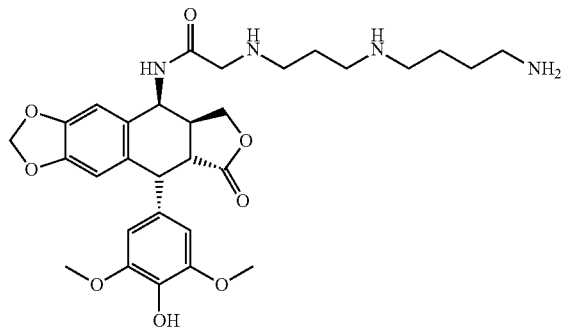

Step 1. Preparation of {3-[benzyloxycarbonyl-(4-benzyloxycarbonylaminobutyl)-amino]-propylamino}-acetic acid ethyl ester

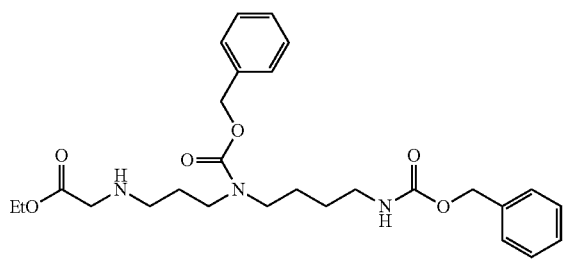 [SMILES: CCOC(=O)CNCCCN(CCCCNC(=O)OCc1ccccc1)C(=O)OCc1ccccc1]

To a solution of 6.35 g (15.4 mmol) of (3-aminopropyl)-(4-benzyloxycarbonyl-aminobutyl)-carbamic acid benzyl ester (*Synth. Commun.* 2005, 35, 1085) in 200 mL of acetonitrile, and 2.6 mL (1.86 g, 15.4 mmol) of triethylamine, there are introduced, with stirring, at ambient temperature, 1.70 mL (2.56 g, 15.4 mmol) of ethyl bromoacetate. Stirring is maintained for 4 hours. The reaction mixture is poured into water and extracted with ethyl acetate. The organic phases are separated off and then dried over sodium sulfate, filtered and evaporated. 7.7 g of an oil are obtained, which is used directly in the following step.

Step 2. Preparation of (benzyloxycarbonyl-{3-[benzyloxycarbonyl-(4-benzyloxy-carbonylaminobutyl)-amino]-propyl}-amino)-acetic acid ethyl ester

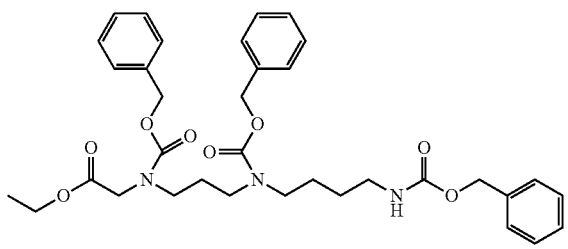 [SMILES: CCOC(=O)CN(CCCN(CCCCNC(=O)OCc1ccccc1)C(=O)OCc1ccccc1)C(=O)OCc1ccccc1]

To a solution of 7.7 g (15.4 mmol) of {3-[benzyloxycarbonyl-(4-benzyloxycarbonyl-aminobutyl)-amino]-propylamino}-acetic acid ethyl ester, as obtained above, in 200 mL of a mixture of water/acetone (1/1) and 1.68 g (20 mmol) of $NaHCO_3$ there are introduced, dropwise with stirring, 2.42 mL (17 mmol) of benzyl chloroformate. Stirring is maintained for 2 hours. The acetone is evaporated off under reduced pressure and then the mixture is acidified with 1N HCl. The mixture is then extracted with ethyl acetate; the organic phases are separated off and dried over anhydrous sodium sulfate, filtered and evaporated. The residue is flash-chromatographed on a silica column using an eluant gradient from pure heptane to a mixture of heptane/AcOEt (60/40). Evaporation of the fractions of interest represents 6 g of a colourless oil. Yield=61%. TLC $SiO_2$, $CH_2Cl_2$/MeOH/$NH_4OH$ (90/10/1) Rf=0.9.

Step 3: Preparation of (benzyloxycarbonyl-{3-[benzyloxycarbonyl-(4-benzyloxy-carbonylaminobutyl)-amino]-propyl}-amino)acetic acid

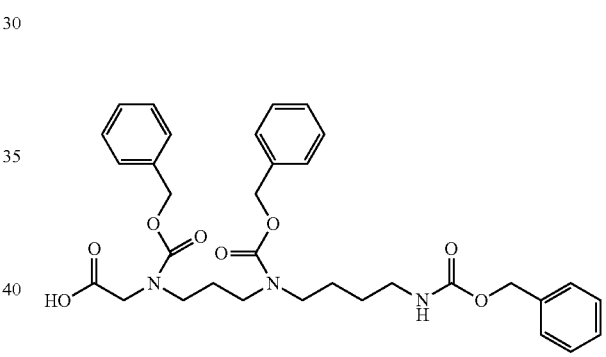

A solution of 5.8 g (9.2 mmol) of (benzyloxycarbonyl-{3-[benzyloxycarbonyl-(4-benzyloxycarbonylaminobutyl)-amino]-propyl}-amino)-acetic acid ethyl ester, as obtained in the preceding step, in 100 mL of ethanol and 13.8 mL (13.7 mmol) of 1N sodium hydroxide solution is heated at reflux for 1 hour. After cooling, 20 mL of 1N hydrochloric acid solution are added and the resulting acid solution is extracted with methylene chloride. The organic phases are separated off, dried over anhydrous sodium sulfate, filtered and evaporated. The residue is flash-chromatographed on silica with an eluant gradient from pure heptane to methylene chloride/MeOH (95/5). Then, after evaporation, 4.7 g of a clear oil are isolated; yield=85%.

TLC; $SiO_2$; $CH_2Cl_2$/MeOH (90/10); Rf=0.35.

Step 4: Preparation of (4-benzyloxycarbonylaminobutyl)-[3-(benzyloxycarbonyl-{[(5S,5aS,8aR,9R)-9-(4-hydroxy-3,5-dimethoxyphenyl)-8-oxo-5,5a,6,8,8a,9-hexa-hydrofuro[3',':6,7]naphtho[2,3-d]-1,3-dioxol-5-ylcarbamoyl]-methyl}-amino)-propyl]-carbamic acid benzyl ester

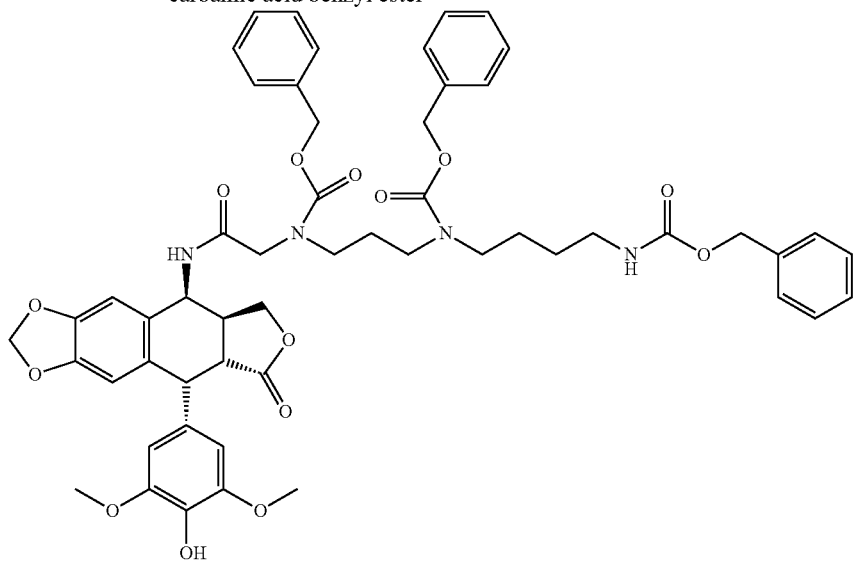

To a suspension of 3.34 g (5.5 mmol) of (benzyloxycarbonyl-{3-[benzyloxycarbonyl-(4-benzyloxycarbonylaminobutyl)-amino]-propyl}-amino)acetic acid, as obtained in the preceding step, and 2.4 g (5.5 mmol) of 4-amino-4'-demethylepipodophyllotoxin hydrochloride in 100 mL of acetonitrile there are added 1.63 mL (11.6 mmol) of triethylamine; the mixture enters into solution with stirring. At this stage there are added 1.77 g (5.5 mmol) of TBTU. The reaction mixture is stirred for 1 hour at ambient temperature. After adding water, the mixture is extracted with ethyl acetate; the organic phases are separated off and washed with NaHCO3 solution and then NaCl solution. The organic phases are again separated off and dried over anhydrous sodium sulfate, filtered and evaporated to obtain 5 g of a white foam. Rapid flash chromatography on silica, with an elution gradient starting from pure heptane to heptane/AcOEt (40/60), makes it possible to obtain 4.6 g of product having a purity of 97% and then another fraction of 0.41 g of 73% purity. These fractions are combined and purified by preparative reverse-phase HPLC. C 18 column; elution with $H_2O/CH_3CN$ (60/40) and then $H_2O/CH_3CN$ (40/60). At this stage there are obtained 4.6 g of compound (yield=84.6%) of 99.8% purity.

TLC: $SiO_2$ $CH_2Cl_2$/MeOH (90/10); Rf=0.75.

Step 5: Preparation of 2-[3-(4-aminobutylamino)-propylamino]-N-[9-(4-hydroxy-3,5-dimethoxyphenyl)-8-oxo-5,5a,6,8,8a,9-hexahydrofuro[3',':6,7]naphtho[2,3-d]-[1,3]dioxol-5-yl]-acetamide hydrochloride The (4-benzyloxycarbonylaminobutyl)-[3-(benzyloxycarbonyl-{[(5S,5aS,8aR,9R)-9-(4-hydroxy-3,5-dimethoxyphenyl)-8-oxo-5,5a,6,8,8a,9-hexahydrofuro[3',4':6,7]naphtho-[2,3-d]-1,3-dioxol-5-ylcarbamoyl]-methyl}-amino)-propyl]-carbamic acid benzyl ester intermediate (4.6 g, 4.7 mmol), as obtained in the preceding step, is stirred under a hydrogen atmosphere in 200 mL of methanol with 460 mg of 10% palladium-on-carbon for 3 hours. At this stage there are added 3 equivalents of HCl/isopropanol. After filtration and evaporation of the solvent, the residue is taken up in absolute ethanol and then filtered and rinsed with ethyl ether. 3.1 g of hydrochloride are isolated (yield=60%). ESI-MS m/z 585.2 (MH+).

EXAMPLE 2

Preparation of 2-[3-[4-(3-aminopropylamino)-butylamino]-propylamino]-N-[9-(4-hydroxy-3,5-dimethoxyphenyl)-8-oxo-5,5a,6,8,8a,9-hexa-hydro-furo[3',4':6,7]naphtho[2,3-d][1,3]dioxol-5-yl]-acetamide, in hydrochloride form. (a=3, b=4, c=3)

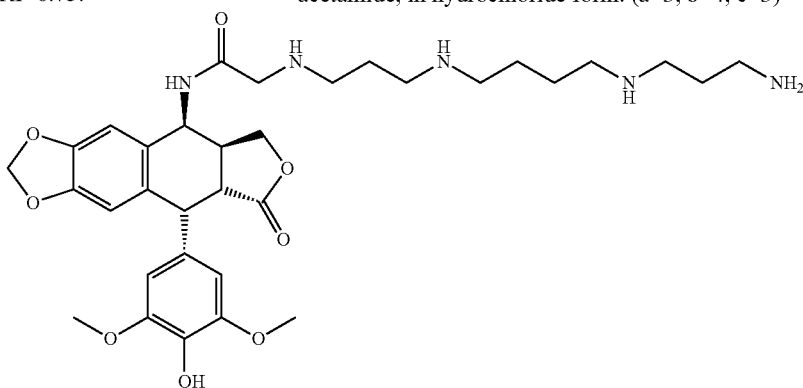

Step 1. Preparation of {benzyloxycarbonyl-[3-(benzyloxycarbonyl-{4-[benzyloxy-carbonyl-(3-benzyloxycarbonylaminopropyl)-amino]-butyl}-amino)-propyl]-amino}-acetic acid ethyl ester

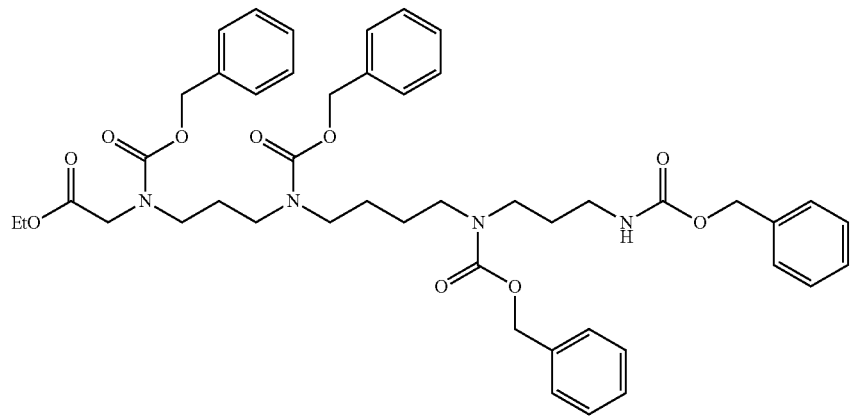 [SMILES: CCOC(=O)CN(CCCN(CCCCN(CCCNC(=O)OCc1ccccc1)C(=O)OCc1ccccc1)C(=O)OCc1ccccc1)C(=O)OCc1ccccc1]

By repeating the procedure indicated in step 1 of Example 1, but this time using {4-[(3-aminopropyl)-benzyloxycarbonylamino]-butyl}-(3-benzyloxycarbonylaminopropyl)-carbamic acid benzyl ester, there is obtained [3-(benzyloxycarbonyl-{4-[benzyloxycarbonyl-(3-benzyloxycarbonylaminopropyl)-amino]-butyl}-amino)-propylamino]-acetic acid ethyl ester in the form of an oil (TLC $SiO_2$ $CH_2Cl_2$/MeOH/$NH_4OH$ (90/9/1) Rf=0.45.

Step 2.

That intermediate is used directly in the conversion that follows, which conversion is analogous in all points to that described in step 2 of Example 1, but using corresponding reactants. There are accordingly obtained 7 g (yield=96.8%) of a colourless oil. TLC $SiO_2$ Heptane/AcOEt (50/50) Rf=0.3.

Step 3. Preparation of {benzyloxycarbonyl-[3-(benzyloxycarbonyl-{4-[benzyloxy-carbonyl-(3-benzyloxycarbonylaminopropyl)-amino]-butyl}-amino)-propyl]-amino}-acetic acid

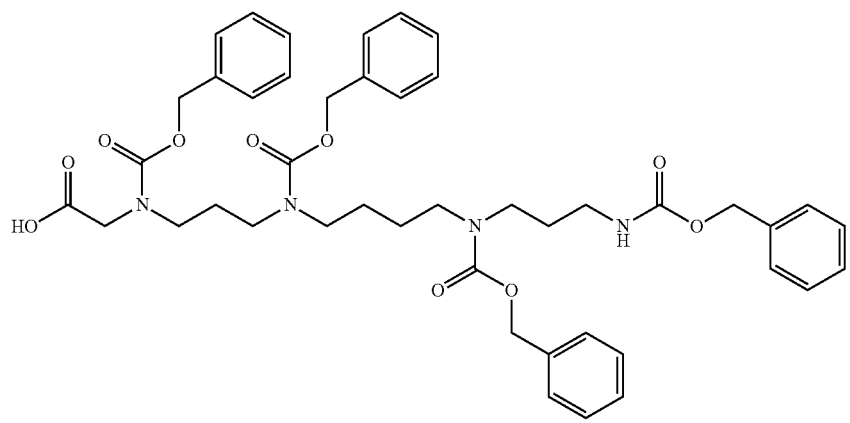 [SMILES: O=C(O)CN(CCCN(CCCCN(CCCNC(=O)OCc1ccccc1)C(=O)OCc1ccccc1)C(=O)OCc1ccccc1)C(=O)OCc1ccccc1]

In accordance with the same procedure as that described in step 3 of Example 1, but using the compound obtained in the preceding step, there are obtained 3.6 g of the corresponding acid (yield=53%) after flash chromatography with an elution gradient from pure $CH_2Cl_2$ to $CH_2Cl_2$/MeOH (95/5).
TLC $SiO_2$, $CH_2Cl_2$/MeOH (95/5) Rf=0.24.

Steps 4 and 5. Preparation of 2-{3-[4-(3-aminopropylamino)-butylamino]-propyl-amino}-N-[9-(4-hydroxy-3,5-dimethoxyphenyl)-8-oxo-5,5a,6,8,8a,9-hexahydrofuro-[3',':6,7]naphtho[2,3-d][1,3]dioxol-5-yl]-acetamide, in hydrochloride form

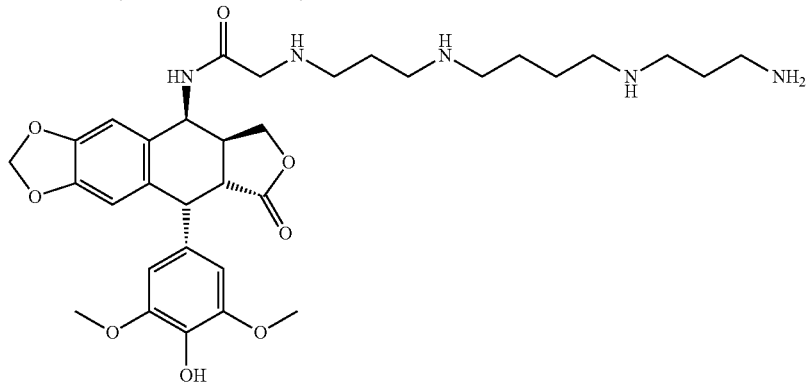

Step 4:

In the same manner as in Example 1, but using the intermediate prepared in step 3 above, coupling with 4-amino-4'-demethylepipodophyllotoxin provides the amide compound in the form of a white foam in a yield 53%. There are then carried out rapid flash chromatography on silica using an elution gradient from heptane to a mixture of $CH_2Cl_2$/MeOH/$NH_4OH$ (90/9/1), then preparative C18 reverse-phase HPLC, eluting with $H_2O$/$CH_3CN$ (60/40) and then $H_2O$/$CH_3CN$ (35/65), and finally evaporation of the acetonitrile and extraction with ethyl acetate.

TLC: $SiO_2$ $CH_2Cl_2$/MeOH (95/05); Rf=0.35.

Step 5:

That intermediate is subjected to debenzylation in accordance with the procedure of step 5 of Example 1. There is then obtained 2-{3-[4-(3-aminopropylamino)-butylamino]-propylamino}-N-[9-(4-hydroxy-3,5-dimethoxyphenyl)-8-oxo-5,5a,6,8,8a,9-hexahydro-furo[3',':6,7]naphtho[2,3-d][1,3]dioxol-5-yl]-acetamide hydrochloride in a yield of 92%.
m.p.=267° C.; TLC $SiO_2$ $CH_2Cl_2$/MeOH/$NH_4OH$ (72/25/3) Rf=0.31; ESI-MS m/z=642.2 (MH+).

EXAMPLE 3

Preparation of 2-{4-[4-(4-aminobutylamino)-butylamino]-butylamino}-N-[9-(4-hydroxy-3,5-dimethoxyphenyl)-8-oxo-5,5a,6,8,8a,9-hexahydro-furo-[3',':6,7]naphtho[2,3-d][1,3]dioxol-5-yl]-acetamide, in hydrochloride form. (a=4, b=4, c=4)

Steps 1 and 2. Preparation of {benzyloxycarbonyl-[4-(benzyloxycarbonyl-{4-[benzyloxycarbonyl-(4-benzyloxycarbonylaminobutyl)-amino]-butyl}-amino)-butyl]-amino}-acetic acid ethyl ester Step 1:

Using the procedure described in step 1 of Example 1, but using (4-aminobutyl)-{4-[benzyloxycarbonyl-(4-benzyloxycarbonylaminobutyl)-amino]-butyl}-carbamic acid benzyl ester, there is obtained [4-(benzyloxycarbonyl-{4-[benzyloxycarbonyl-(4-benzyloxycarbonylaminobutyl)-amino]-butyl}-amino)-butylamino]-acetic acid ethyl ester in the form of an oil.

TLC $SiO_2$ $CH_2Cl_2$/MeOH/$NH_4OH$ (90/9/1) Rf=0.48.

Step 2:

That intermediate is used directly in the step that follows, in which the procedure is in all points analogous to that described in step 2 of Example 1. Using the corresponding reactants, there is accordingly obtained {benzyloxycarbonyl-4-[(benzyloxycarbonyl-{4-[benzyloxycarbonyl-(4-benzyloxycarbonylaminobutyl)-amino]-butyl}-amino)-butyl]-amino}-acetic acid ethyl ester as a colourless oil in a yield of 75%.

TLC $SiO_2$ $CH_2Cl_2$/MeOH/$NH_4OH$ (95/4.5/0.5) Rf=0.35.

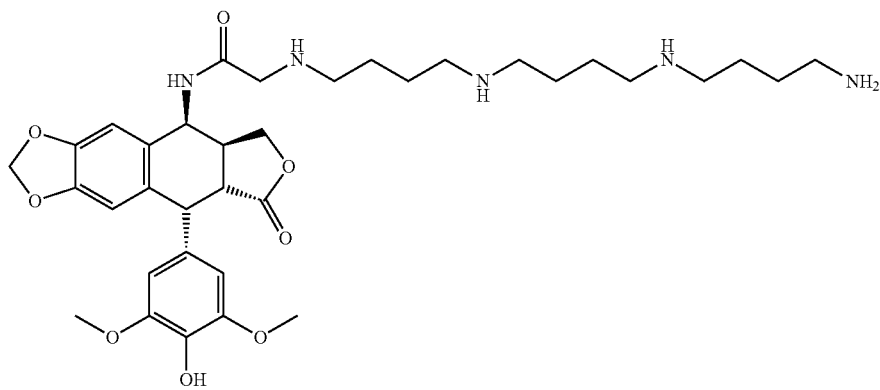

Step 3. Preparation of {benzyloxycarbonyl-[4-(benzyloxycarbonyl-{4-[benzyloxy-carbonyl-(4-benzyloxycarbonylaminobutyl)-amino]-butyl}-amino)-butyl]-amino}-acetic acid

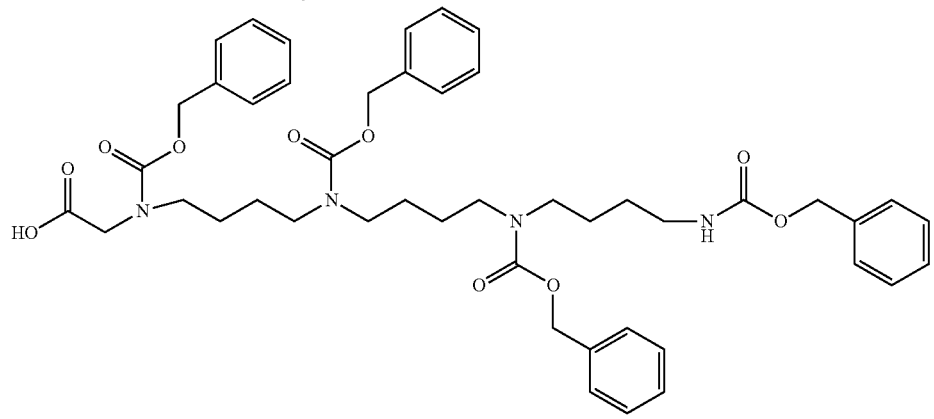 [SMILES: O=C(O)CN(CCCCN(CCCCN(CCCCNC(=O)OCc1ccccc1)C(=O)OCc1ccccc1)C(=O)OCc1ccccc1)C(=O)OCc1ccccc1]

In accordance with the procedure as described in step 3 of Example 1 but using the compound obtained above, the corresponding acid is obtained in a yield of 88% following flash chromatography with an elution gradient from pure CH$_2$Cl$_2$ to CH$_2$Cl$_2$/MeOH (90/10).

TLC SiO$_2$, CH$_2$Cl$_2$/MeOH (90/0) Rf=0.53.

Steps 4 and 5. Preparation of 2-{4-[4-(4-aminobutylamino)-butylamino]-butyl-amino}-N-[9-(4-hydroxy-3,5-dimethoxyphenyl)-8-oxo-5,5a,6,8,8a,9-hexahydrofuro-[3',':6,7]naphtho[2,3-d][1,3]dioxol-5-yl]-acetamide, in hydrochloride form Step 4:

In the same manner as in step 4 of Example 1, but using the intermediate prepared in the step above, the coupling of that intermediate with 4-amino-4'-demethyl-epipodophyllotoxin provides the amide compound in the form of a white foam in a yield of 62%. After rapid flash chromatography on silica using a gradient from CH$_2$Cl$_2$ to a mixture of CH$_2$Cl$_2$/MeOH (95/5), then preparative C18 reverse-phase HPLC eluting with H$_2$O/CH$_3$CN (60/40) and then H$_2$O/CH$_3$CN (30/70), followed by evaporation of the acetonitrile and extraction with ethyl acetate.

TLC: SiO$_2$ CH$_2$Cl$_2$/MeOH/NH$_4$OH (95/4.5/0.5); Rf=0.24, to obtain the intermediate used directly in the following step.

Step 5:

That intermediate is subjected to debenzylation in accordance with the procedure of step 5 of Example 1. There is then obtained 2-{4-[4-(4-aminobutylamino)-butylamino]-butylamino}-N-[9-(4-hydroxy-3,5-dimethoxyphenyl)-8-oxo-5,5a,6,8,8a,9-hexahydro-furo[3',4':6,7]naphtho[2,3-d][1,3]dioxol-5-yl]-acetamide in a yield of 78%.

m.p.=263° C.; DCI-MS/CH4 m/z=670.5 (MH+).

EXAMPLE 4

Preparation of 2-[4-(3-aminopropylamino)-butylamino]-N-[9-(4-hydroxy-3,5-dimethoxyphenyl)-8-oxo-5,5a,6,8,8a,9-hexahydrofuro[3',':6,7]-naphtho[2,3-d][1,3]dioxol-5-yl]-acetamide, in hydrochloride form. (a=4, b=3, R=H)

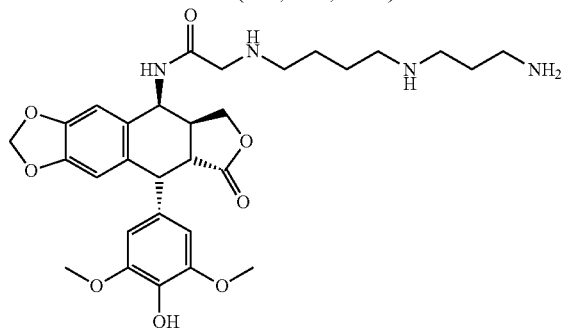

Steps 1 and 2. Preparation of benzyloxycarbonyl-{-4-[benzyloxycarbonyl-(3-benzyl-oxycarbonylaminopropyl)-amino]-butyl}-amino)-acetic ethyl ester

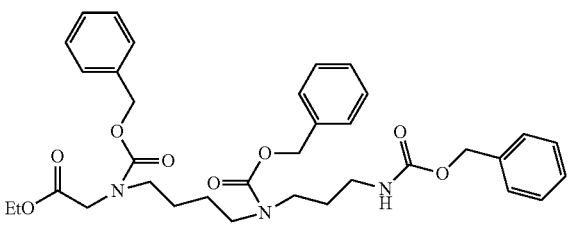 [SMILES: CCOC(=O)CN(CCCCN(CCCNC(=O)OCc1ccccc1)C(=O)OCc1ccccc1)C(=O)OCc1ccccc1]

Step 1:

Using the procedure indicated in step 1 of Example 1, but using {3-[(4-aminobutyl)-benzyloxycarbonylamino]-propyl}-carbamic acid benzyl ester, there is obtained {4-[benzyloxycarbonyl-(3-benzyloxycarbonylaminopropyl)-amino]-butylamino}-acetic acid ethyl ester in the form of an oil.

TLC SiO$_2$ CH$_2$Cl$_2$/MeOH/NH$_4$OH (95/4.5/0.5) Rf=0.28, ESI-MS m/z=500.3 (MH+).

Step 2:

The intermediate obtained above is used directly in the conversion that follows, which is in all points analogous to that described in step 2 of Example 1. There is accordingly obtained benzyloxycarbonyl-{-4-[benzyloxycarbonyl-(3-benzyloxycarbonylamino-propyl)-amino]-butyl}-amino)-acetic acid ethyl ester in the form of a colourless oil.

(TLC SiO$_2$ CH$_2$Cl$_2$/MeOH/NH$_4$OH (95/4.5/0.5) Rf=0.39. APCI-MS m/z=634.3 (MH+)

Step 3. Preparation of (benzyloxycarbonyl-{4-[benzyloxycarbonyl-(3-benzyloxycarbonylaminopropyl)-amino]-butyl}-amino)-acetic acid

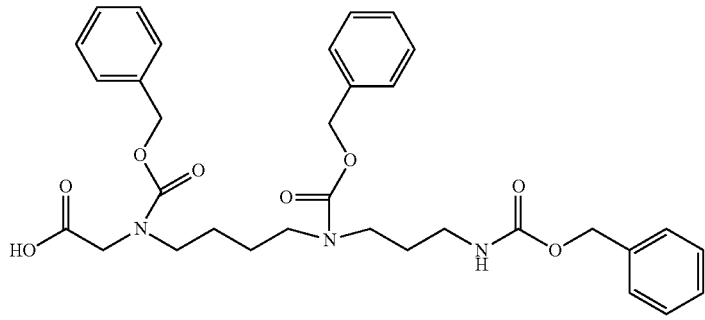 [SMILES: O=C(O)CN(CCCCN(CCCNC(=O)OCc1ccccc1)C(=O)OCc1ccccc1)C(=O)OCc1ccccc1]

In accordance with the same procedure as that described in step 3 of Example 1, but using the compound obtained in the step above, the corresponding acid is obtained, by acid extraction, in a yield of 86%
TLC SiO$_2$, CH$_2$Cl$_2$/MeOH (90/10) Rf=0.48.

Steps 4 and 5: Preparation of 2-[4-(3-aminopropylamino)-butylamino)-N-[9-(4-hydroxy-3,5-dimethoxyphenyl)-8-oxo-5,5a,6,8,8a,9-hexahydrofuro[3',':6,7]-naphtho[2,3-d][1,3]dioxol-5-yl]-acetamide, in hydrochloride form

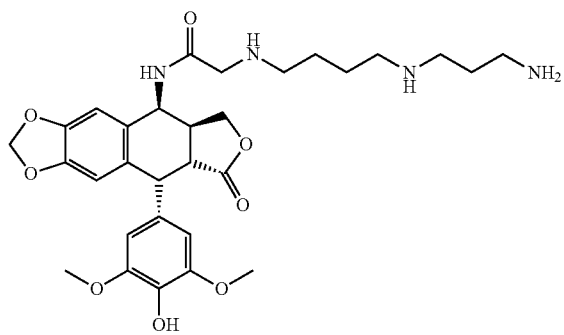

Step 4:
In the same manner as in step 4 of Example 1, but using the intermediate prepared in the step above, the coupling of that intermediate with 4-amino-4'-demethyl-epipodophyllotoxin provides the amide compound in the form of a white foam in a yield of 48%. After rapid flash chromatography on silica using a gradient starting from heptane to AcOEt. then preparative C18 reverse-phase HPLC eluting with H$_2$O/CH$_3$CN (60/40) and then H$_2$O/CH$_3$CN (35/65), and finally evaporation of the acetonitrile and extraction with ethyl acetate. TLC: SiO$_2$ CH$_2$Cl$_2$/MeOH/NH$_4$OH (95/4.5/0.5); Rf=0.30

Step 5:
The intermediate obtained is subjected to debenzylation in accordance with the procedure of step 5 of Example 1. There is then obtained 2-[4-(3-aminopropylamino)-butylamino]-N-[9-(4-hydroxy-3,5-dimethoxyphenyl)-8-oxo-5,5a,6,8,8a,9-hexahydrofuro [3',4':6,7]-naphtho[2,3-d][1,3]dioxol-5-yl]-acetamide hydrochloride in a yield of 79%.
m.p.=197° C.; ESI-MS m/z=585.3 (MH+).
B) Method Using t-Butyloxycarbonyl Groups.

EXAMPLE 5

Preparation of 2-{3-[4-(3-aminopropylamino)-butylamino]-propyl-amino}-N-[9-(4-hydroxy-3,5-dimethoxyphenyl)-8-oxo-5,5a,6,8,8a,9-hexahydrofuro-[3',':6,7]naphtho[2,3-d][1,3]dioxol-5-yl] acetamide, in hydrochloride form. (a=3, b=4, c=3)

Step 1. Preparation of 3-(t-butyloxycarbonyl-{4-[t-butyloxycarbonyl-(3-t-butyloxy-carbonylaminopropyl)-amino]-butyl}-amino)-propylamino]-acetic acid ethyl ester

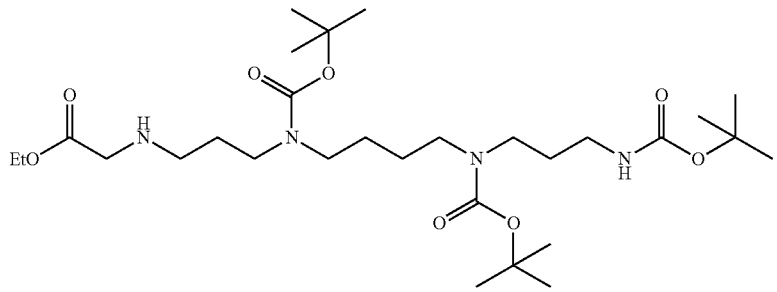 [SMILES: CCOC(=O)CNCCCN(CCCCN(CCCNC(=O)OC(C)(C)C)C(=O)OC(C)(C)C)C(=O)OC(C)(C)C]

To a solution of 5.11 g of tri-BOC-spermine (*Tet. Let.* 1998, 39, 439) (10 mmol, 1 eq) in 120 mL of acetonitrile there are added 1.7 mL of triethylamine (12 mmol, 1.2 eq). There are then introduced into the resulting solution, rapidly and with stirring, 1.13 mL of ethyl bromoacetate (10 mmol, 1 eq). After stirring for 1 hour at normal temperature, the reaction mixture is discharged into water saturated with NaCl (300 mL), and extraction with ethyl acetate (2×200 mL) is carried out. After drying of the organic phases, filtration and evaporation, the residue obtained is purified by flash chromatography on SiO$_2$ (eluting with a gradient starting from pure heptane to pure CH$_2$Cl$_2$, and then with CH$_2$Cl$_2$/MeOH—90/10). 3.35 g of a colourless oil are obtained (yield=56%) TLC Rf=0.57 (CH$_2$Cl$_2$/MeOH—90/10).

Step 2. Preparation of {t-butyloxycarbonyl-[3-(t-butyloxycarbonyl-{4-[t-butyloxy-carbonyl-(3-t-butyloxycarbonylaminopropyl)-amino]-butyl}-amino)-propyl]-amino}-acetic acid ethyl ester

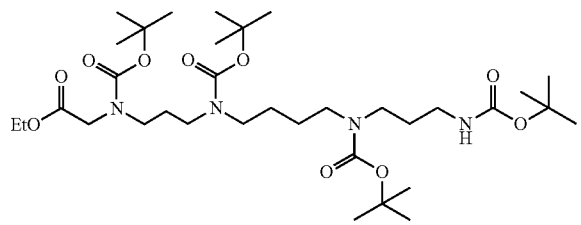

To a solution, at ambient temperature, of 3.35 g of the intermediate obtained in step 1 above (5.7 mmol, 1 eq) in 60 mL of THF, there are added 1 mL of triethylamine (6.8 mmol, 1.2 eq) and then, with stirring, a solution of 1.36 g of BOC$_2$O (6.2 mmol, 1.1 eq), and stirring is carried out for 2 hours. The reaction mixture is then discharged into water (300 mL), and extraction with ethyl acetate (3×200 mL) is carried out. The organic phases, after being dried over sodium sulfate and filtered, are evaporated and then flash-chromatographed on SiO$_2$ (eluting with a gradient from pure heptane to pure ethyl acetate) to provide 2.52 g of a colourless oil. Yield=64% TLC Rf=0.43 (SiO$_2$ Heptane/AcOEt—50/50).

Step 3. Preparation of {t-butyloxycarbonyl-[3-(t-butyloxycarbonyl-{4-[t-butyloxy-carbonyl-(3-t-butyloxycarbonylaminopropyl)-amino]-butyl}-amino)-propyl]-amino}-acetic acid

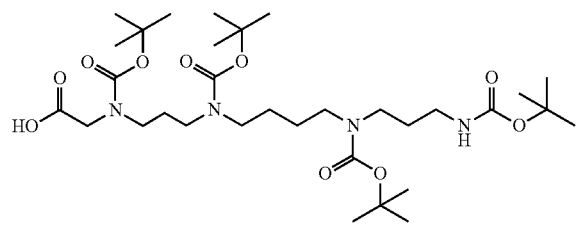 [SMILES: CC(C)(C)OC(=O)NCCCN(CCCCN(CCCN(CC(=O)O)C(=O)OC(C)(C)C)C(=O)OC(C)(C)C)C(=O)OC(C)(C)C]

The ester intermediate obtained in step 2 (2.52 g, 3.6 mmol, 1 eq) is heated at reflux, with stirring, in 50 mL of a mixture of EtOH/H$_2$O and 5.5 mL of 1N sodium hydroxide solution for 3 hours. The mixture is discharged into ice-cold water (300 mL) and acidification with 1N HCl (5.6 mL) is carried out. After extracting with CH$_2$Cl$_2$, drying over Na$_2$SO$_4$, filtering and evaporating, purification by flash chromatography on SiO$_2$ is carried (elution gradient from pure heptane to pure CH$_2$Cl$_2$ and then to CH$_2$Cl$_2$/MeOH—90/10). There are then obtained 2.27 g of tetra-BOC-spermine-acetic acid in the form of a colourless oil. Yield=94%.

TLC Rf 0.4 (SiO$_2$ CH$_2$Cl$_2$/MeOH—90/10). (lit. *Tet. Let.* 1997, 38, 3219).

Steps 4 and 5: Preparation of 2-{3-[4-(3-aminopropylamino)-butylamino]-propylamino}-N-[9-(4-hydroxy-3,5-dimethoxyphenyl)-8-oxo-5,5a,6,8,8a,9-hexa-hydrofuro[3',':6,7]naphtho[2,3-d][1,3]dioxol-5-yl]-acetamide, in hydrochloride form Step 4:

To a stirred solution of 670 mg of 4-amino-4'-demethyl-epipodophyllotoxin (1.54 mmol, 1 eq) and 1.02 g of the intermediate obtained in step 3 (1.54 mmol, 1 eq) in 100 mL of acetonitrile, at ambient temperature, there is added 0.45 mL of triethylamine (3.28 mmol, 2 eq). Complete dissolution is observed. There is then added 0.5 g of TBTU (1.54 mmol, 1 eq) and stirring is maintained for 2 hours. The reaction mixture is then discharged into 300 mL of water, and extraction with ethyl acetate (3×100 mL) is carried out. After drying of the organic phases over Na$_2$SO$_4$, filtration and evaporation, the residue is flash-chromatographed on SiO$_2$ (gradient elution from pure heptane to AcOEt). The compound obtained, which has a purity of 92%, is again chromatographed by preparative HPLC (C18, Sunfire OBD, 10p) and eluted with CH$_3$CN/H$_2$O—50/50 to CH$_3$CN/H$_2$O—65/35. The aqueous phase obtained is re-extracted with ethyl acetate, dried and evaporated to provide 800 mg of a colourless oil, which is used directly in the next step. Yield=50%. TLC SiO$_2$ Rf 0.4 (CH$_2$Cl$_2$/MeOHNH$_4$OH—90/9/1).

Step 5:

To a solution of 800 mg of the compound obtained above (0.77 mmol, 1 eq) in 20 mL of EtOH, there are added, with stirring, 20 mL of isopropanol solution saturated with HCl. Stirring is maintained for 5 hours. The mixture is evaporated in vacuo and taken up in 10 ml of absolute EtOH with stirring. A precipitate is obtained, which is filtered off and dried in vacuo. (500 mg). Purification by preparative HPLC(C18, Sunfire, OBD, 10µ) eluted with CH$_3$CN/H$_2$O/AcONH$_4$ 1.54 g/L, AcOH 2 mL/L, makes it possible to obtain a pure compound, the solution of which is lyophilised. The lyophilisate is taken up in 10 mL of MeOH and is then acidified to pH 3 using a solution of HCl isopropanol. The solution of the hydrochloride obtained is evaporated and then taken up in absolute EtOH. There are obtained 190 mg (yield=32%) of 2-{3-[4-(3-aminopropylamino)-butyl-amino]-propylamino}-N-[9-(4-hydroxy-3,5-dimethoxyphenyl)-8-oxo-5, 5a,6,8,8a,9-hexa-hydrofuro[3',4':6,7]naphtho[2,3-d][1,3]dioxol-5-yl]acetamide, in hydrochloride form.

The invention claimed is:

1. A process for the preparation of a (poly)aminoalkylaminoacetamide derivative of epipodophyllotoxin, of formula 1

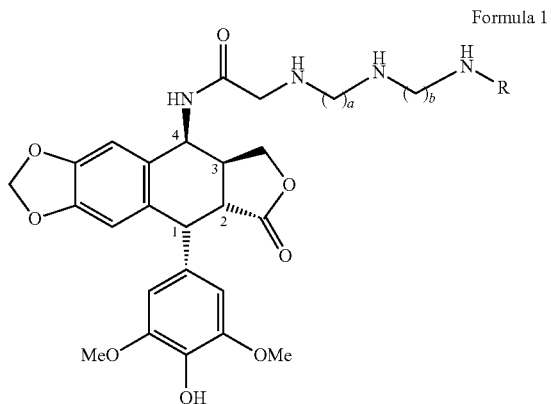

Formula 1 or a pharmaceutically acceptable salt thereof, wherein R represents a hydrogen atom or a group —$(CH_2)_c$—$NH_2$, wherein a, b and c each independently represent 2, 3, 4 or 5, comprising peptide coupling of 4-amino-4'-demethylepipodophyllotoxin of formula 4bis

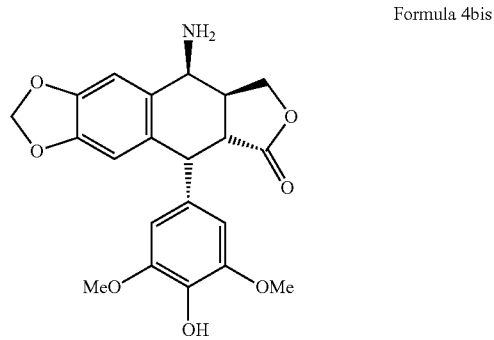

Formula 4bis with a compound of formula 6

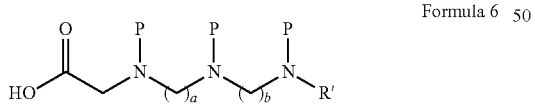

Formula 6 wherein P represents a protecting group for the amine function selected from benzyloxycarbonyl and t-butyloxycarbonyl, and R' represents H or a chain —$(CH_2)_c$—NHP, wherein c represents 2, 3, 4 or 5, wherein O-benzotriazol-1-yl-N,N,N',N'-tetramethyluronium tetrafluoroborate (TBTU) is employed as a coupling agent, and wherein the coupling reaction is performed without using an excess of reactant.

2. The process according to claim 1, wherein the compound of formula 1 is obtained as its hydrochloride salt.

3. The process for the preparation of 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide, as its hydrochloride salt, according to claim 1, comprising peptide coupling between 4-amino-4'-demethylepipodophyllotoxin and {benzyloxycarbonyl-[3-(benzyloxycarbonyl-{4-[benzyloxycarbonyl-(3-benzyloxycarbonylaminopropyl)-amino]-butyl}-amino)-propyl]-amino}-acetic acid or 3-(t-butyloxycarbonyl-{4-[t-butyloxycarbonyl-(3-t-butyloxycarbonylaminopropyl)-amino]-butyl}-amino)-propylamino]-acetic acid.

4. The process for the preparation of 2-[3-(4-aminobutylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide hydrochloride, according to claim 1, comprising peptide coupling between 4-amino-4'-demethylepipodophyllotoxin and (benzyloxycarbonyl-{3-[benzyloxy-carbonyl-(4-benzyloxycarbonylaminobutyl)-amino]-propyl}-amino)acetic acid or (t-butyloxycarbonyl-{3-[t-butyloxycarbonyl-(4-t-butyloxycarbonylaminobutyl)-amino]-propyl}-amino)acetic acid.

5. The process for the preparation of 2-{4-[4-(4-aminobutylamino)-buty amino]-butylamino}N-[9-(4-hydroxy-3,5-dimethoxyphenyl)-8-oxo-5,5a,6,8,8a,9-hexahydrofuro[3',':6,7]naphtho[2,3-d][1,3]dioxol-5-yl]-acetamide tetrahydrochloride, according to claim 1, comprising peptide coupling between 4-amino-4'-demethylepipodophyllotoxin and {benzyloxycarbonyl-[4-(benzyloxycarbonyl-{4-[benzyloxycarbonyl-(4-benzyloxycarbonylaminobutyl)-amino]-butyl}-amino)-butyl]-amino}-acetic acid or {t-butyloxycarbonyl-[4-(t-butyloxycarbonyl-{4-[t-butyloxycarbonyl-(4-t-butyloxycarbonylaminobutyl)-amino]-butyl}-amino)-butyl]-amino}-acetic acid.

6. The process for the preparation of 2-[4-(3-aminopropylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide hydrochloride, according to claim 1, comprising peptide coupling between 4-amino-4'-demethylepipodophyllotoxin and (benzyloxycarbonyl-{4-[benzyloxy-carbonyl-(3-benzyloxycarbonylaminopropyl)-amino]-butyl}-amino)-acetic acid or t-butyloxycarbonyl-{4-[t-butyloxycarbonyl-(3-t-butyloxycarbonylaminopropyl)-amino]-butyl}-amino)-acetic acid.

7. The process for the preparation of a derivative of formula 1, according to claim 1, comprising the following steps:
a) attaching an acetic moiety to a primary-amine-containing reactant of formula 5

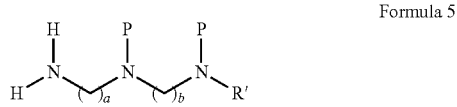

Formula 5 wherein P represents a protecting group selected from benzyloxycarbonyl and t-butyloxycarbonyl,
with the aid of an alkyl haloacetate;
b) protecting the secondary amine of the compound obtained in the preceding step a), by means of a protecting group P, wherein P represents a benzyloxycarbonyl group or a t-butyloxycarbonyl group;
c) saponification of the compound obtained in step b), in a basic medium, to obtain the polyaminoacetic acid of formula 6

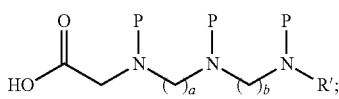
Formula 6 d) peptide coupling of the polyaminoacetic acid of formula 6 obtained in step c), with 4-amino-4'-demethylepipodophyllotoxin, employing O-benzotriazol-1-yl-N,N,N', N'-tetramethyluronium tetrafluoroborate (TBTU) as a coupling agent; and e) removing the protecting groups P from the compound obtained in the preceding step to arrive at the derivative of formula 1.

8. The process according to claim 7, wherein the alkyl haloacetate used in step a) is an ethyl bromo-, chloro- or iodo-acetate.

9. The process for the preparation of 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide, as its hydrochloride salt, according to claim 7, comprising the following steps:

a) attaching an acetic moiety to {4-[(3-aminopropyl)-benzyloxy-carbonylamino]butyl}-(3-benzyloxycarbonylaminopropyl)-carbamic acid benzyl ester or tri-BOC-spermine with the aid of ethyl bromoacetate to obtain [3-(benzyloxycarbonyl-{4-[benzyloxycarbonyl-(3-benzyloxy-carbonylaminopropyl)-amino]-butyl}-amino)-propyl]-amino}-acetic acid ethyl ester or 3-(t-butyloxycarbonyl-{4-[t-butyloxycarbonyl-(3-t-butyloxy-carbonylaminopropyl)-amino]-butyl}-amino)-propylamino]-acetic acid ethyl ester;

b) protecting the secondary amine of the compound obtained in the preceding step a), by means of a protecting group which is either a benzyloxycarbonyl group or a t-butyloxycarbonyl group;

c) saponification of the compound obtained in step b), in a basic medium, to obtain either {benzyloxycarbonyl-[3-(benzyloxycarbonyl-{4-[benzyl-oxycarbonyl-(3-benzyloxycarbonylaminopropyl)-amino]-butyl}-amino)-propyl]-amino}-acetic acid or {t-butyloxycarbonyl-[3-(t-butyloxy-carbonyl]-{4-[t-butyloxycarbonyl-(3-t-butyloxycarbonylaminopropyl)-amino]-butyl}-amino)-propyl]-amino}-acetic acid;

d) peptide coupling of the compound obtained in step with 4-amino-4'-demethylepipodophyllotoxin; and e) removing the benzyloxycarbonyl or t-butyloxycarbonyl protecting groups from the compounds obtained in the preceding step.

10. The process for the preparation of 2-[3-(4-aminobutylamino)-propylamino]-N-[9-(4-hydroxy-3,5-dimethoxyphenyl)-8-oxo-5,5a,6,8,8a,9-hexahydrofuro[3',4':6,7]naphtho 2,3d][[1,3]dioxol-5-yl]-acetamide, as its hydrochloride salt, according to claim 7, wherein the compound of formulae 5 and 6 used in steps a) and c) are those wherein a represents 3, b represents 4 and R' represents H.

11. The process for the preparation of 2-{4-[4-(4-aminobutylamino)-butylamino]-butylamino}-N-[9-(4-hydroxy-3,5-dimethoxyphenyl)-8-oxo-5,5a,6,8,8a,9-hexahydrofuro[3',4': 6,7]naphtho[2,3-d][1,3]dioxool-5-yl]-acetamide, as its hydrochloride salt, according to claim 7, wherein the compounds of formulae 5 and 6 used in steps a) and c) are those wherein a represents 4, b represents 4 and c represents 4.

12. The process for the preparation of 2-[4-(3-aminopropylamino)-butylamino]-N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-acetamide, as its hydrochloride salt, according to claim 7, wherein the compounds of formulae 5 and 6 used in steps a) and c) are those wherein a represents 4, b represents 3 and R' represents H.

13. The process according to claim 1, wherein the compound of formula 6

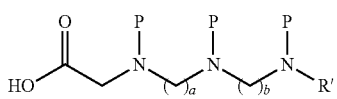
Formula 6 is prepared by a process comprising the following steps:
a) attaching an acetic moiety to the primary-amine-containing reactants of formula 5

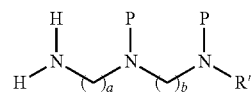
Formula 5 wherein P represents a protecting group selected from benzyloxycarbonyl and t-butyloxycarbonyl, with the aid of an alkyl haloacetate;

b) protecting the secondary amine of the compound obtained in the preceding step a), by means of a protecting group P, wherein P represents a benzyloxycarbonyl group or a t-butyloxycarbonyl group;

c) saponification of the compound obtained in step b), in a basic medium, to obtain the polyaminoacetic acid of formula 6.

14. The process according to claim 13, wherein the alkyl haloacetate used in step a) is an ethyl bromo-, chloro- or iodo-acetate.

15. The process accordingly to claim 13, wherein the compound of formula 6 is selected from: {benzyloxycarbonyl-[3-(benzyloxycarbonyl-{4-[benzyloxycarbonyl-(3-benzyloxycarbonylaminopropyl)-amino]-butyl}-amino)-propyl]-amino}-acetic acid and {t-butyloxycarbonyl-[3-(t-butyloxycarbonyl-{4-[t-butyloxycarbonyl-(3-t-butyloxycarbonylaminopropyl)-amino]-butyl}-amino)-propyl]-amino}-acetic acid, which process comprises the following steps:

a) attaching, an acetic moiety to the primary-amine-containing reactant of formula 5 wherein, a represents 3, b represents 4 and R' represents —(CH$_2$)$_3$—NHP, wherein P represents a benzyloxycarbonyl group or a t-butyloxycarbonyl group, with the aid of ethyl bromoacetate;

b) protecting the secondary amine of the compound obtained in the preceding step a), by means of a protecting group which is analogous to that selected in step a); and c) saponification of the compound obtained in step b).

16. The process according to claim 13, wherein a represents 3, b represents 4 and R' represents H.

17. The process according to claim 13, wherein a represents 4, b represents 4 and c represents 4.

18. The process according to claim 13, wherein a represents 4, b represents 3 and R' represents H, according to claim 13, wherein the compound of formula 5 used in step a) is that wherein a represents 4, b represents 3 and R' represents H.

* * * * *

UNITED STATES PATENT AND TRADEMARK OFFICE
CERTIFICATE OF CORRECTION

PATENT NO.         : 8,664,409 B2
APPLICATION NO.    : 12/733864
DATED              : March 4, 2014
INVENTOR(S)        : Guminski et al.

It is certified that error appears in the above-identified patent and that said Letters Patent is hereby corrected as shown below:

In the Claims

Column 28, Line 26, Claim 5: "[3',':6,7]" should be --[3',4':6,7]--.

Column 29, Line 49, Claim 9: "step" should be --step c),--.

Column 29, Line 57, Claim 10: "[2,3d][[1,3]" should be --[2,3d] [1,3]--.

Column 29, Line 63, Claim 11: "dioxool" should be --dioxol--.

Signed and Sealed this
Twentieth Day of May, 2014

Michelle K. Lee
*Deputy Director of the United States Patent and Trademark Office*